United States Patent
Tandon

(10) Patent No.: US 10,589,096 B2
(45) Date of Patent: Mar. 17, 2020

(54) SYSTEMS AND METHODS FOR NETWORK BASED NEUROSTIMULATION OF COGNITIVE PROCESSES

(71) Applicant: THE BOARD OF REGENTS OF THE UNIVERSITY OF TEXAS SYSTEM, Austin, TX (US)

(72) Inventor: Nitin Tandon, Houston, TX (US)

(73) Assignee: THE BOARD OF REGENTS OF THE UNIVERSITY OF TEXAS SYSTEM, Austin, TX (US)

( * ) Notice: Subject to any disclaimer, the term of this patent is extended or adjusted under 35 U.S.C. 154(b) by 212 days.

(21) Appl. No.: 15/496,444

(22) Filed: Apr. 25, 2017

(65) Prior Publication Data
US 2017/0304623 A1    Oct. 26, 2017

Related U.S. Application Data

(60) Provisional application No. 62/327,188, filed on Apr. 25, 2016.

(51) Int. Cl.
| | |
|---|---|
| *A61N 1/36* | (2006.01) |
| *A61N 1/05* | (2006.01) |
| *A61B 5/00* | (2006.01) |
| *A61B 8/08* | (2006.01) |
| *A61B 6/00* | (2006.01) |
| *A61B 5/055* | (2006.01) |
| *A61B 6/03* | (2006.01) |

(52) U.S. Cl.
CPC ........ *A61N 1/36082* (2013.01); *A61B 5/0042* (2013.01); *A61B 5/055* (2013.01); *A61N 1/0531* (2013.01); *A61N 1/0534* (2013.01); *A61N 1/36132* (2013.01); *A61N 1/36153* (2013.01); *A61N 1/36157* (2013.01); *A61N 1/36171* (2013.01); *A61N 1/36175* (2013.01); *A61B 6/037* (2013.01); *A61B 6/501* (2013.01); *A61B 8/0808* (2013.01)

(58) Field of Classification Search
CPC ............ A61N 1/36082; A61N 1/36132; A61N 1/0534; A61N 1/0531; A61N 1/36157; A61N 1/36153; A61N 1/36171; A61N 1/36175; A61B 5/055; A61B 5/0042; A61B 6/037; A61B 8/0808; A61B 6/501
See application file for complete search history.

(56) References Cited

U.S. PATENT DOCUMENTS

| | | |
|---|---|---|
| 6,920,359 B2 | 7/2005 | Meadows et al. |
| 8,024,049 B1 | 9/2011 | Gilson et al. |
| 8,412,332 B2 | 4/2013 | Massoud-Ansari et al. |

(Continued)

FOREIGN PATENT DOCUMENTS

WO    WO 2004/037342    5/2004

OTHER PUBLICATIONS

Kim, K., et al., "A Network Approach for Modulating Memory Processes Via Direct and Indirect Brain Stimulation: Toward a Causal Approach for the Neural Basis of Memory", *Neurobiology of Learning and Memory* 134 (2016): 162-177.

*Primary Examiner* — Mark Bockelman
(74) *Attorney, Agent, or Firm* — Parker Highlander PLLC

(57) ABSTRACT

This invention relates generally to systems and methods for multifocal direct brain stimulation to enhance cognitive processing, such as but not limited to stimulation-induced modulation of memory.

18 Claims, 4 Drawing Sheets
(4 of 4 Drawing Sheet(s) Filed in Color)

(56) References Cited

U.S. PATENT DOCUMENTS

| | | | |
|---|---|---|---|
| 8,489,185 B2* | 7/2013 | Kilgard | A61N 1/36014 607/2 |
| 8,644,940 B2 | 2/2014 | Forsell | |
| 8,649,876 B2 | 2/2014 | Sarvazyan | |
| 8,944,985 B2 | 2/2015 | Bonmassar et al. | |
| 10,149,618 B1 | 12/2018 | Tandon et al. | |
| 2013/0289385 A1 | 10/2013 | Lozano | |
| 2014/0180358 A1 | 6/2014 | Giftakis et al. | |
| 2014/0350634 A1 | 11/2014 | Grill et al. | |
| 2015/0148863 A1 | 5/2015 | Lee | |

* cited by examiner

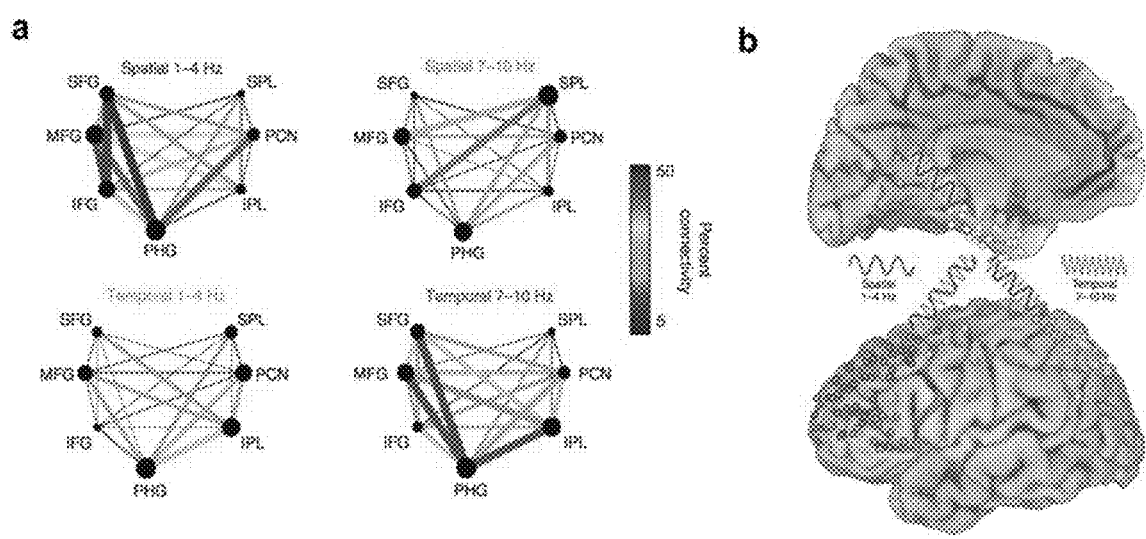
FIGS. 1A-B
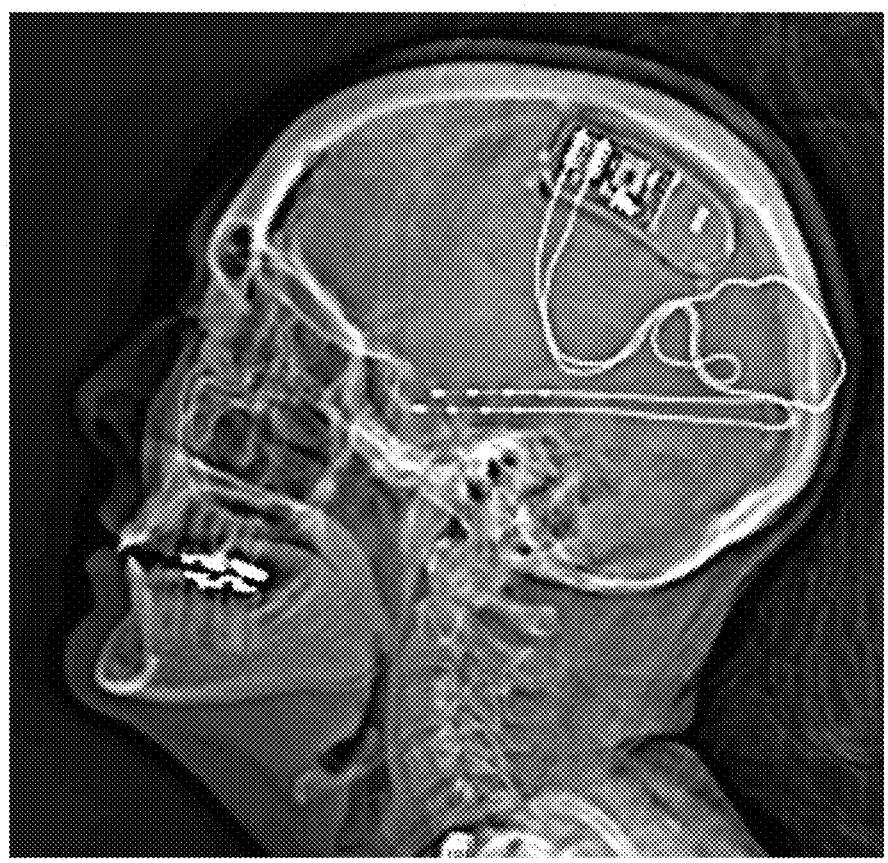
FIG. 2

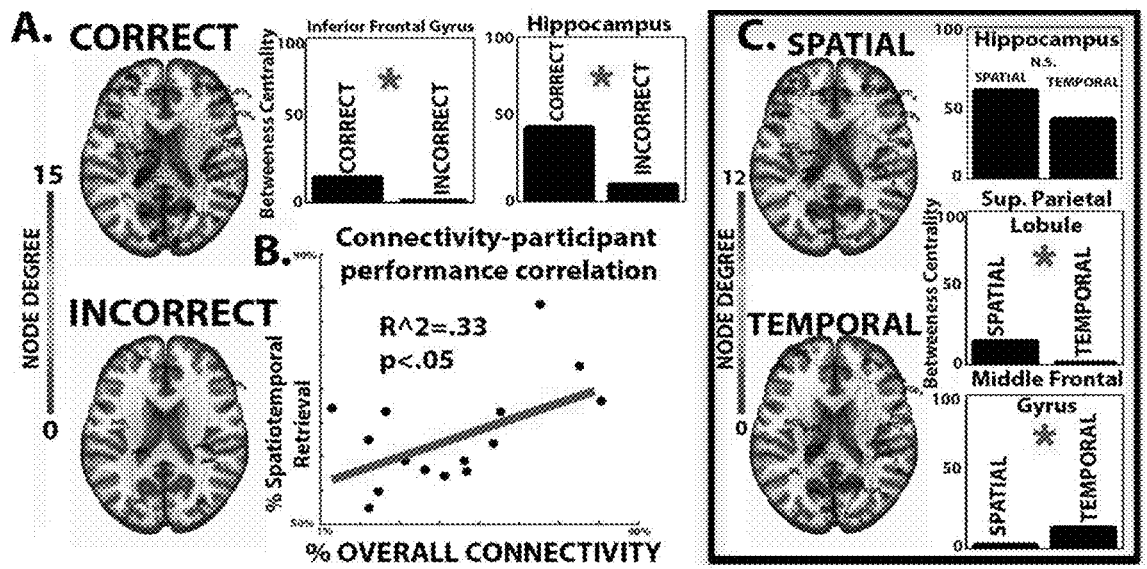
FIGS. 3A-C
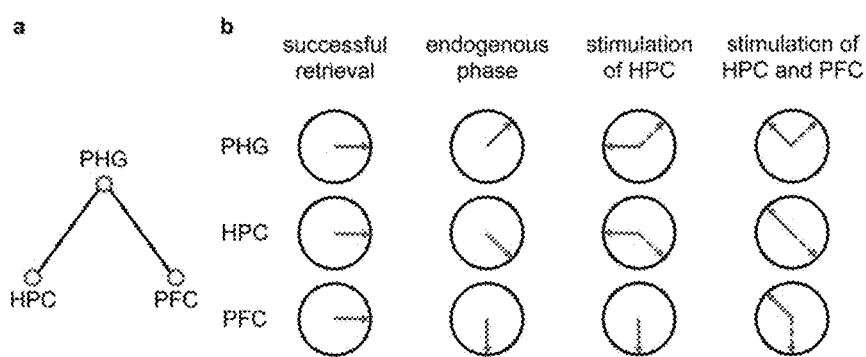
FIGS. 4A-B

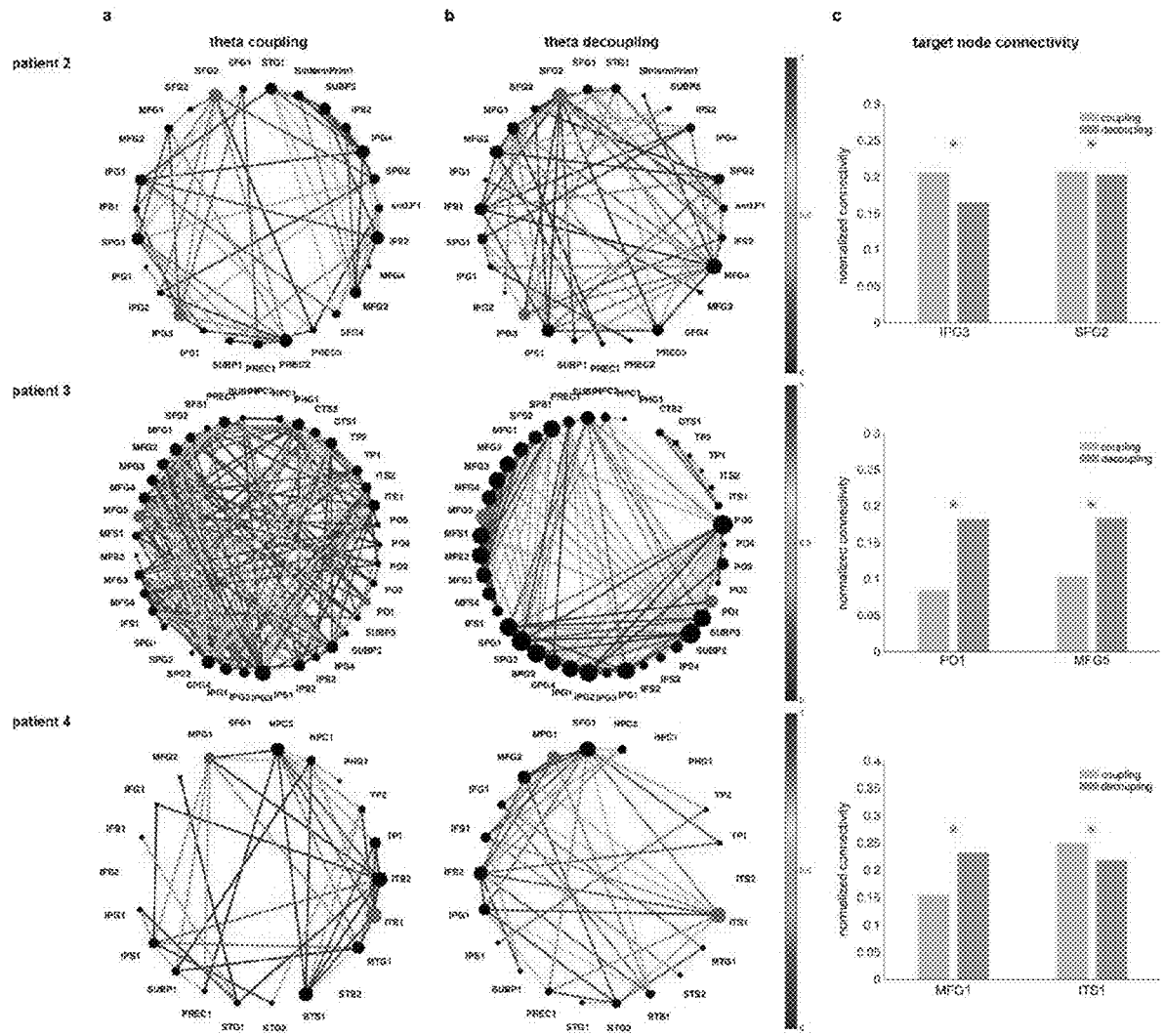
FIGS. 6A-C

SYSTEMS AND METHODS FOR NETWORK BASED NEUROSTIMULATION OF COGNITIVE PROCESSES

CROSS-REFERENCE TO RELATED APPLICATIONS

This application claims priority to U.S. Provisional Patent Application Ser. No. 62/327,188 filed Apr. 25, 2016, the entire contents of which are incorporated herein by reference.

STATEMENT REGARDING FEDERALLY SPONSORED RESEARCH OR DEVELOPMENT

This invention was made with U.S. Government support under Grant Nos. R21NS087527 and KL2 RR024149 awarded by the National Institutes of Health. The government has certain rights in the invention.

COPYRIGHT NOTICE

A portion of the disclosure of this patent document contains material that is subject to copyright protection. The copyright owner has no objection to the facsimile reproduction by anyone of the patent document or the patent disclosure, as it appears in the U.S. Patent and Trademark Office patent file or records, but otherwise reserves all copyright rights whatsoever.

FIELD OF THE INVENTION

This invention relates generally to systems and methods for multifocal brain stimulation to enhance cognitive processing, such as, but not limited to cortical stimulation to enhance memory, reduce memory loss, aid in language production, name retrieval.

BACKGROUND OF THE INVENTION

Cognitive processes are brain operations that allow us to perform complex functions that are the very essence of being human—examples include but are not limited to memory, language, control over emotions, resolving conflicting information, reading, making decisions, puzzle solving etc. These functions are subject to various disorders produced by brain injury, aging, and to mental health disorders that primarily affect learning, memory, perception, and problem solving, and include amnesia, dementia, and delirium. Additionally psychiatric conditions like anxiety disorders, mood disorders, and psychotic disorders can also have an effect on cognitive functions but in these cases the loss of cognitive function is not the primary (causal) symptom.

Described herein are systems and methods for multifocal direct brain stimulation to enhance cognitive processing, for which there is a longstanding and unmet need.

SUMMARY OF THE INVENTION

In a first embodiment, the invention provides a method of enhancing a cognitive process in a subject having a disease or neurological injury, the method comprising applying an intracranial electrical stimulation to a plurality of nodes in different regions of the brain of the subject, wherein the intracranial electrical stimulation is applied at nodes in different regions of the brain of the subject that are active during an effective cognitive process. In some aspects, the method additionally comprises monitoring a cognitive process of the brain.

In certain aspects, applying the intracranial electrical simulation is phase-synchronized at a first frequency band. In other aspects, applying the intracranial electrical simulation to the plurality of nodes in different regions of the brain of the subject induces coherent oscillations between the nodes.

In several aspects, the different regions of the brain of the subject comprise a broad network in many distinct brain regions. An example would be stimulation the hippocampus (HPC) region, coupled with a second region connected with this—such as the parahippocampal (PHG) region, and a third region more distant but connected region of the brain the prefrontal cortex (PFC). In further aspects, applying the intracranial electrical simulation to the plurality of nodes comprises: applying a first electrical signal to a first node in the first region of the brain; applying a second electrical signal to a second node in the second region of the brain; applying a third electrical signal to a third node in the third region of the brain; and inducing coherent oscillations between the first, second and third nodes. Notably, this can be extended beyond three to much larger numbers of nodes (e.g. up to 50), by scaling the technology used for stimulation. In some aspects, application of the first electrical signal, the second electrical signal and the third electrical signal to the first node, the second node and the third node is phase-synchronized at a first frequency band. In some specific aspects, the first, second and third nodes comprise subdural electrodes (SDEs).

In additional aspects, the first, second and third nodes may be probed with depth electrodes (DEs). In further aspects, the method may additionally comprise performing a recording procedure to obtain the patterns of activity of different regions of the brain of the subject that are active during the cognitive process of interest. In other aspects, the method may additionally comprise performing an imaging procedure to obtain an image of a non-subject brain and identifying the different regions of the subject or non-subject brain that are active during the effective cognitive process. In certain aspects, identifying the different regions of the brain of the subject that are active during the effective cognitive process comprises using anatomical landmarks or population maps of brain activity or placing intracranial electrodes to localize and characterize brain areas engaged in a given cognitive process. In further particular aspects, the imaging procedure may be magnetic resonance imaging (MRI), functional magnetic resonance imaging (fMRI), x-ray, ultrasound imaging, or positron emission tomography (PET).

Brain recordings obtained using DEs or subdural grid electrodes (SDEs) or microelectrodes or any combination thereof during the performance of cognitive processes either for a single epoch or averaged over multiple trials may be recorded. These may then be delivered as patterned stimulation to mimic the recordings. In this manner the amplitude and the frequencies of the recordings may be replayed into single or multiple nodes of the nervous system using intracranial electrodes. Such an approach may induce the occurrence of the cognitive process without the individual's volition. Variations in the playback of these recordings may be systematically used to alter the cognitive percept. Such an approach may also be used to induce changes in the behavior of a brain network that may be long lasting. Specifically, it may be used to affect a variety of brain illnesses that affect cognition, including but not limited to dementia, memory loss, dyslexia, dis-inhibition, aphasia, visual loss, acalculia, depression or cause mental illnesses such as depression, anxiety or obsessive compulsive disorders.

A further embodiment of the invention provides a system for enhancing a cognitive process in a brain of a subject, the system comprising a plurality of nodes and a controller configured to provide intracranial electrical simulation to the plurality of nodes, wherein the electrical stimulation is applied at nodes in different regions of the brain of the subject that are active during an effective cognitive process. In some aspects, the system is configured to monitor the cognitive process of the brain of the subject. In several aspects, the controller is configured to provide intracranial electrical simulation to the plurality of nodes that is phase-synchronized at a first frequency band. In other aspects, the controller is configured to provide intracranial electrical simulation to the plurality of nodes that induces coherent oscillations between the nodes in the plurality of nodes.

In further aspects, the different regions of the brain of the subject comprise a first region of the brain in a hippocampus (HPC) region, a second region of the brain in a parahippocampal (PHG) region, and a third region of the brain in a prefrontal cortex (PFC) region, and so on. Network based stimulation can target multiple brain areas (nodes) that are involved in the function that needs to be modulated. In certain aspects, the controller may be configured to apply a first electrical signal to a first node in the first region of the brain, apply a second electrical signal to a second node in the second region of the brain, apply a third electrical signal to a third node in the third region of the brain, and induce coherent oscillations between the first, second and third nodes. In specific aspects, application of the first electrical signal, the second electrical signal and the third electrical signal to the first node, the second node and the third node is phase-synchronized at a first frequency band. In some particular aspects, the first, second and third nodes are probed or recorded from using subdural electrodes (SDEs). In other aspects, the first, second and third nodes comprise depth electrodes (DEs).

In some aspects of the embodiments described herein, the intracranial electrical simulation has a frequency between 2 and 1000 Hz, or more particularly 20 and 200 Hz. For example, the intracranial electrical simulation may have a frequency of approximately 130 Hz or approximately 80 Hz. In certain aspects, the intracranial electrical simulation may have a voltage between 0.01 volts and 10.0 volts, or more particularly 0.1 volts and 10.0 volts. In certain aspects, the intracranial electrical simulation may have a voltage between 1.0 volts and 10.0 volts. In some specific aspects, the intracranial electrical simulation has a voltage between 3.0 volts and 3.5 volts. In particular aspects, the intracranial electrical simulation has a current value between 0.01 mA and 20 mA. In other aspects, the intracranial electrical simulation has a voltage of less than 7.0 volts. In some aspects, the intracranial electrical simulation current is either based on voltage or current, based on the specific area being stimulated. In several aspects, the intracranial electrical simulation has a pulse width of 50-1000 µs (microseconds) or 45-450 µs (microseconds) or 10 µs (microseconds) to 500 milliseconds. For example, the intracranial electrical simulation may have a pulse width of approximately 100 µs or approximately 90 µs (microseconds). In some aspects, the intracranial electrical simulation has either square wave pulses, or sine waves pulses or combinations thereof. In particular aspects, charge balancing—anodal and cathodal stimulation occurring at the same site—can be performed as needed to minimize the potential for charge deposition and to prevent injury to neural tissues. In certain aspects, the effective cognitive process comprises spatial recall, temporal recall, speech production, reading, language comprehension, arithmetic, attention or cognitive control, sensory feedback related to movement and/or coordinated locomotion.

Certain aspects include a system for enhancing a cognitive process in a brain of a subject, the system comprising a plurality of nodes; and a controller configured to provide intracranial electrical simulation to the plurality of nodes, where the electrical stimulation is applied at nodes in different regions of the brain of the subject that are active during an effective cognitive process. In some aspects, the system is configured to monitor the cognitive process of the brain of the subject. In particular aspects, the controller is configured to provide intracranial electrical simulation to the plurality of nodes that is phase-synchronized at a one or more frequency bands. In certain aspects, the controller is configured to provide intracranial electrical simulation to the plurality of nodes that induces coherent oscillations between the nodes in the plurality of nodes. In specific aspects, the different regions of the brain of the subject comprise a first region of the brain in a hippocampus (HPC) region, a second region of the brain in a parahippocampal (PHG) region, and a third region of the brain in a prefrontal cortex (PFC) region.

In particular aspects, the controller is configured to: apply a first electrical signal to a first node in the first region of the brain; apply a second electrical signal to a second node in the second region of the brain; apply a third electrical signal to a third node in the third region of the brain; and induce coherent oscillations between the first, second and third nodes. In some aspects, the controller is configured to induce coherent oscillations between the first, second and third nodes by closely spacing an onset of the first, second and third electrical signals to the first, second, and third nodes. In certain aspects, application of the first electrical signal, the second electrical signal and the third electrical signal to the first node, the second node and the third node is phase-synchronized at a first frequency band. In some aspects, the first, second and third nodes comprise subdural electrodes (SDEs). In particular aspects, the first, second and third nodes comprise depth electrodes (DEs).

In certain aspects, the intracranial electrical simulation has a frequency between 2 and 1000 Hz, or more particularly 20 and 200 Hz. In specific aspects, the intracranial electrical simulation has a frequency of approximately 80 Hz or 130 Hz. In some aspects, the intracranial electrical simulation has a voltage between 0.1 volts and 10.0 volts, or more particularly between 1.0 and 10.0 volts. In particular aspects, the intracranial electrical simulation has a current value between 0.01 mA and 20 mA. In certain aspects, the intracranial electrical simulation has a voltage less than 7.0 volts, or more particularly between 3.0 volts and 3.5 volts. In some aspects, the intracranial electrical simulation is either based on voltage or current, based on the specific area being stimulated.

In particular aspects, the intracranial electrical simulation has a pulse width of 10-µs (microseconds) to 500 milliseconds or 45-450 µs (microseconds). In some aspects, the intracranial electrical simulation has either square wave pulses, or sine waves pulses or combinations thereof. In specific aspects, charge balancing—anodal and cathodal stimulation occurring at the same site—can be performed as needed to minimize the potential for charge deposition and to prevent injury to neural tissues. In certain aspects, the intracranial electrical simulation has a pulse width of approximately 90 µs (microseconds).

In particular aspects, the effective cognitive process comprises spatial recall, temporal recall, speech production, reading, language comprehension, arithmetic, attention or cognitive control. In certain aspects, the effective cognitive process comprises coordinated locomotion or sensory feedback related to movement.

The following presents a simplified summary of the invention in order to provide a basic understanding of some aspects of the invention. This summary is not an extensive overview of the invention. It is intended to neither identify key or critical elements of the invention nor delineate the scope of the invention. Its sole purpose is to present some concepts of the invention in a simplified form as a prelude to the more detailed description that is presented later.

The present invention together with the above and other advantages may best be understood from the following detailed description of the embodiments of the invention and as illustrated in the drawings. The following description, while indicating various embodiments of the invention and numerous specific details thereof, is given by way of illustration and not of limitation. Many substitutions, modifications, additions or rearrangements may be made within the scope of the invention, and the invention includes all such substitutions, modifications, additions or rearrangements.

BRIEF DESCRIPTION OF THE FIGURES

The patent or application file contains at least one drawing executed in color. Copies of this patent or patent application publication with color drawing(s) will be provided by the Office upon request and payment of the necessary fee.

The drawings accompanying and forming part of this specification are included to depict certain aspects of the invention. A clearer impression of the invention, and of the components and operation of systems provided with the invention, will become more readily apparent by referring to the exemplary, and therefore non-limiting, embodiments illustrated in the drawings, wherein identical reference numerals designate the same components. Note that the features illustrated in the drawings are not necessarily drawn to scale.

FIGS. 1A-B illustrate spectral fingerprinting and multiplexing in memory retrieval. (a) The network exhibits stronger phase synchronization at a lower frequency band (1-4 Hz) for retrieval of spatial information and at a higher frequency band (7-10 Hz) for retrieval of temporal information. (b) The same network is involved in retrieval of spatial and temporal memory, but nodes communicate via selective frequency bands for distinct types of information.

FIG. 2 is an illustrative example of a patient with a NeuroPace device. This patient and bilateral MTLE and MTS—two electrodes placed along the long axis of the hippocampus for chronic recording and closed loop neuromodulation. No significant improvement was noted in either seizure frequency or memory.

FIGS. 3A-C illustrate correct vs. incorrect and spatial vs. temporal fMRI retrieval networks—Task-related fMRI and graph theory demonstrate higher connectivity for correct vs. incorrect retrieval and different connectivity for spatial vs. temporal retrieval with 4 different brains of utilizing intraoperative imaging in conjunction with a 3D cortical model for mapping the locations of implanted electrodes.

FIGS. 4A-B illustrate the network stimulation concept. Sect(a) a simplified network with three nodes: hippocampus (HPC), parahippocampus (PHG) and prefrontal cortex (PFC). HPC has direct projections to and from PHG, but not with PFC. (b) hypothetical phase vectors and their coherence among these regions. 'Successful retrieval' requires coherent oscillations. 'Endogenous phase'—these regions are less likely to be in-phase with one another when the network is not engaged. 'Stimulation of HPC' will reset the endogenous oscillatory phase (dotted lines) of HPC as well as nodes directly connected with it, i.e., PHG, to a new phase (solid line) Yet, it would take synchronized 'Stimulation of HPC and PFC' to bring the network into a coherent phase optimized for task performance.

FIGS. 6A-C illustrate a map demonstrating how networks are constructed.

DETAILED DESCRIPTION OF THE INVENTION

Figure 5:
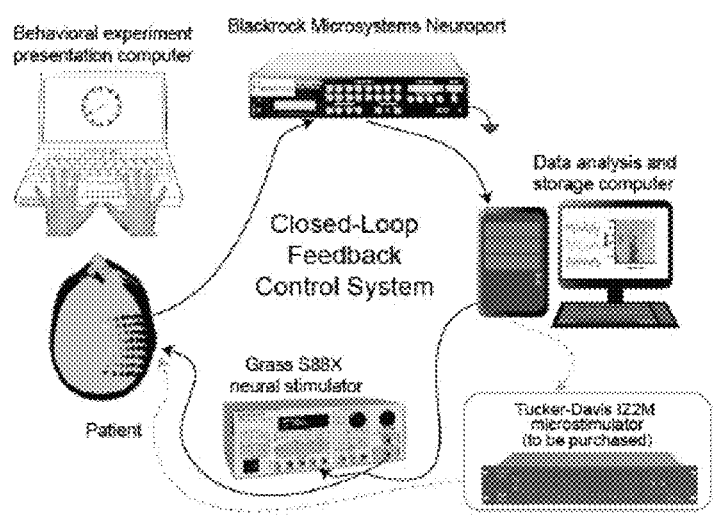
FIG. 5 illustrates an embodiment of an externalized closed loop system in which the electrons hardware and computers are optimized to record ongoing brain activity and then replay the signal back to the brain to "induce" cognitive processes artificially.

The detailed description set forth below is intended as a description of the presently exemplified systems, methods, devices and compositions which are provided in accordance with aspects of the present invention, and is not intended to represent the only forms in which the invention may be practiced or utilized. It is to be understood, however, that the same or equivalent functions and components may be accomplished by different embodiments also intended to be encompassed within the spirit and scope of the invention.

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the exemplified systems, methods, devices and materials are now described.

In this disclosure, the use of the singular includes the plural, the word "a" or "an" means "at least one", and the use of "or" means "and/or", unless specifically stated otherwise. Furthermore, the use of the term "including", as well as other forms, such as "includes" and "included", is not limiting. Also, terms such as "element" or "component" encompass both elements and components comprising one unit and elements or components that comprise more than one unit unless specifically stated otherwise.

As used herein, the term "about," when used in conjunction with a percentage or other numerical amount, means plus or minus 10% of that percentage or other numerical amount. For example, the term "about 80%," would encompass 80% plus or minus 8%.

The section headings used herein are for organizational purposes only and are not to be construed as limiting the subject matter described. All documents, or portions of documents, cited in this application, including, but not limited to, patents, patent applications, articles, books, and treatises, are hereby expressly incorporated herein by reference in their entirety for any purpose. In the event that one or more of the incorporated literature and similar materials defines a term in a manner that contradicts the definition of that term in this application, this application controls.

As used herein, and unless otherwise indicated, the terms "cognitive process" and "cognitive processing" refer to mental processes and processing, including for example, perception, memory, language, arithmetic, problem solving, and abstract thinking.

As used herein, and unless otherwise indicated, the terms "cognitive process disorder" and "cognitive processing disorder" for which the present methods and systems may be used to improve one or more parameters include, but are not limited to improving memory, restoring speech, enhancing self-control, enabling abstract thought and facilitating sensori-motor performance. As used herein, and unless otherwise indicated, the terms "treat," "treating," "treatment" and "therapy" contemplate an action that occurs while a patient is suffering from a cognitive processing disorder, such as but not limited to memory loss associate with and which reduces the severity of one or more symptoms or effect of such a disorder. Where the context allows, the terms "treat," "treating," and "treatment" also refers to actions taken toward ensuring that individuals at increased risk of a cognitive process disorder and which reduces the severity are able to receive appropriate surgical and/or other medical intervention prior to onset of a cognitive process disorder, such as but not limited to neuronal dysfunction, a neuron mediated disorder, ocular disorder or cardiac disorder and which reduces the severity.

As used herein, and unless otherwise indicated, the terms "prevent," "preventing," and "prevention" contemplate an action that occurs before a patient begins to suffer from a cognitive process disorder, that delays the onset of, and/or inhibits or reduces the severity of a cognitive process disorder.

As used herein, and unless otherwise indicated, the terms "manage," "managing," and "management" encompass preventing, delaying, or reducing the severity of a recurrence of a cognitive process disorder in a patient who has already suffered from such a disease, disorder or condition. The terms encompass modulating the threshold, development, and/or duration of the disorder that involves electrically active cells or changing how a patient responds to the disorder that involves electrically active cells or the maintenance and/or establishment of a desirable membrane potential across the membrane of a cell.

As used herein, and unless otherwise specified, a "therapeutically effective amount" of a compound is an amount sufficient to provide any therapeutic benefit in the treatment or management of a disorder that involves a cognitive process disorder, or to delay or minimize one or more symptoms associated with a cognitive process disorder. A therapeutically effective amount of a compound means an amount of the compound, alone or in combination with one or more other therapies and/or therapeutic agents that provide any therapeutic benefit in the treatment or management of a cognitive process disorder.

The term "therapeutically effective amount" can encompass an amount that alleviates a cognitive process disorder, improves or reduces a cognitive process disorder or improves overall therapy, or enhances the therapeutic efficacy of another therapeutic agent.

As used herein, and unless otherwise specified, a "prophylactically effective amount" of a therapy is an amount sufficient to prevent or delay the onset of a cognitive process disorder or one or more symptoms associated with a disorder that involves electrically active cells or prevent or delay its recurrence. A prophylactically effective amount of a therapy means an amount of the therapy, alone or in combination with one or more other treatment and/or prophylactic agent that provides a prophylactic benefit in the prevention of a cognitive process disorder. The term "prophylactically effective amount" can encompass an amount that prevents a cognitive process disorder, improves overall prophylaxis, or enhances the prophylactic efficacy of another prophylactic agent. The "prophylactically effective amount" can be prescribed prior to, for example, the development of a cognitive process disorder.

As used herein, "patient" or "subject" includes mammalian organisms which are capable of suffering from a cognitive process disorder, as described herein, such as human and non-human mammals, for example, but not limited to, rodents, mice, rats, non-human primates, companion animals such as dogs and cats as well as livestock, e.g., sheep, cow, horse, etc.

Presently, various different approaches exist to electrically stimulate the brain to help alleviate degenerative diseases and nervous system disorders, such as Parkinson's disease and epilepsy. For example, electrical stimulation can provide an effective treatment for patients when surgical lesioning of brain tissue is not a suitable option as well as when patients are not sufficiently responsive to other treatment modalities, such as drug therapy.

Some of the different types of electrical stimulation treatments include vagal nerve stimulation, cerebellar stimulation, and direct brain stimulation. One major advantage of electrical stimulation over lesioning procedures (e.g., pallidotomy and thalamotomy) is that the electrical stimulation can be reversible and can be adjustable. For example, brain stimulation can be implemented with no destruction of brain tissue and the stimulator can be removed, if needed. Additionally, the stimulation can be adjusted (e.g., increased, minimized or turned off or otherwise modified) to achieve better clinical effects for each patient.

Direct brain stimulation (DBS) is a neurosurgical procedure involving the implantation of a medical device such as a neurostimulator (sometimes referred to as a 'brain pacemaker'), which sends electrical impulses, through implanted electrodes, to specific parts of the brain (brain nucleus) for the treatment of movement and affective disorders. The abbreviation "DBS" has also been used to refer to "Deep" brain stimulation as in select deep seated brain regions. DBS has provided therapeutic benefits for otherwise-treatment-resistant movement and affective disorders such as Parkinson's disease, essential tremor, dystonia, chronic pain, major depression and obsessive-compulsive disorder (OCD). DBS alters brain activity in a controlled manner and its effects are reversible. The US Food and Drug Administration (FDA) has approved the marketing of DBS as a treatment for essential tremor, Parkinson's disease, dystonia and OCD. DBS is also used in research studies to treat chronic pain, PTSD, epilepsy, depression and others.

DBS is effective for some patients, potential for serious complications and side effects exist. Electrical stimulation of the brain is a unique tool to perturb endogenous neural signals, allowing us to evaluate the necessity of given neural processes to cognitive processing. An important issue, gaining increasing interest in the literature, is whether and how stimulation can be employed to selectively improve or disrupt declarative memory processes. There is no particular reason why brain stimulation must target deep-seated regions such as the basal ganglia, thalamus or brainstem. Indeed given the distributed nature of cortical processing that underpins cognitive operations, targeting the cortex is indeed the optimal strategy.

In general, direct brain stimulation involves the precise electrical stimulation of specific brain structures using implanted electrodes. Examples of deep brain stimulation are provided at least in, patent publications U.S. Pat. Nos. 6,920,359, 8,944,985, US20140350634, U.S. Pat. Nos. 8,024,049, 8,412,332, 8,649,876 and US20130289385. Recently, there has been significant work in the area of electrical stimulation of the subthalamic nucleus (STN) in which miniature electrodes are placed into the STN on one or both sides of the brain. STN is a structure located deep within the brain that has been found to control many aspects of normal motor function. Electrical stimulation of the STN effectively jams or blocks the abnormal circuitry of the brain, such as in the case of Parkinson's disease or epilepsy. Various types of stimulators can be utilized to electrically stimulate the desired multiple foci according to an aspect of the present invention. In some embodiments stimulators may be programmable. In other embodiments stimulators may be implantable. Examples of brain stimulators appear in WO/2004/037342, 20140180358, 20150148863 and 8644940, among others. Therefore, in some embodiments, the present invention relates to the stimulation of regions of a patient's brain for therapeutic purposes and, in particular, to a therapeutic brain stimulation system to stimulate the brain electrically by advancing electrodes into specific brain regions to be stimulated simultaneously.

In other embodiments, brain stimulation includes a direct electrical stimulation, TMS (transcranial magnetic stimulation) and TES (transcranial electrical stimulation), particularly tDCS (transcranial direct current stimulation) and tRNS (transcranial random noise stimulation).

In the case of tDCS, particularly, a weak direct current is continuously applied through two touching electrodes on the scalp. This causes fine alterations in membrane potential and changes in firing rate of cortical nerve cells, thus influencing an excitement level of the cortical nerve cells. To be more specific, the excitement level increases or decreases depending on a polarity of the electrodes. In the case of stimulating an anode (the anode is in the neighborhood of the cell body or dendrite of the cortical nerve cells), depolarization takes place by an increased membrane potential and firing rate, thus augmenting the excitement of the cortical nerve cells. In the case of stimulating a cathode, nerve cells become hyperpolarized as a result of the decreased membrane potential and firing rate.

Thus brain stimulating systems are embodied in different forms and should not be construed as limited to the embodiments set forth herein. Rather, these embodiments are provided so that this disclosure will be thorough and complete, and will fully convey the scope of the brain stimulating system to those skilled in the art. The same reference numbers indicate the same components throughout the specification.

Implantable medical devices, such as electrical stimulators or therapeutic agent delivery devices may be used in different therapeutic applications, such as direct brain stimulation (DBS) to a tissue site within a patient's brain.

A medical device may be used to deliver therapy to a patient to treat a variety of symptoms or patient conditions such as chronic pain, tremor, Parkinson's disease, other types of movement disorders, seizure disorders (e.g., epilepsy), obesity or mood disorders. In some therapy systems, an external or implantable electrical stimulator delivers electrical therapy to a target tissue site within a patient with the aid of one or more implanted electrodes, which may be deployed by medical leads or on a housing of the stimulator.

Various anti-seizure therapies and other therapies can attempt to suppress brain activity to reduce seizures or produce another therapeutic effect. Stimulation can cause episodes of after-discharge. The chronic trigging of after-discharge events is not regarded as a therapy goal.

Epilepsy and other conditions can be characterized by inappropriate bioelectrical brain activity within one or more brain structures. For example, some seizures associated with temporal lobe epilepsy can arise in the hippocampus of the brain. Accordingly, for at least some patients, reducing the bioelectrical activity level within the hippocampus may reduce problematic cortical activity and may be desirable for managing a seizure disorder. The reduced bioelectrical activity level within the hippocampus may help mitigate symptoms of the seizure disorder, such as by lowering the likelihood of the occurrence of a seizure, reducing the severity or duration of seizures, and/or reducing the frequency of seizures.

Direct brain stimulation is one option for therapeutically addressing a seizure disorder by lowering the activity within the hippocampus or other brain area. For example, a lead can be implanted with one or more electrodes contacting the hippocampus or other brain area targeted for stimulation therapy. Electrical stimulation delivered from the one or more electrodes can change the intrinsic bioelectrical electrical activity of the hippocampus or other targeted brain area. One of the challenges of hippocampal direct brain stimulation for epilepsy is selection of stimulation parameters for best treatment. Currently, continuous low-voltage stimulation can be used for therapy. In some cases, therapeutic electrical stimulation of the hippocampus can be delivered at a lower energy level relative to therapeutic electrical stimulation of the some other brain targets because of the sensitivity of the hippocampus to stimulation. The paradox is that stimulation of the hippocampus can cause after-discharges, which are brief seizure-like episodes of bioelectrical activity that occur during and/or immediately following electrical stimulation. Hippocampal direct brain stimulation is preferably managed for some patients to maintain the intensity of the therapy at a level that therapeutically addresses the seizure disorder while not causing unintended brain events. For example, some stimulation parameters may fail to lower bioelectrical activity or otherwise therapeutically address the seizure condition while some other stimulation parameters may be associated with unintended side effects. As mentioned above, electrical stimulation at some energy levels can cause an after-discharge in the hippocampus.

Sensing bioelectrical activity in the brain is a useful tool for calibrating electrical stimulation parameters. For example, the bioelectrical activity of the hippocampus or other brain area can be monitored in real-time to provide feedback on the level of reduction of brain activity contributing to the seizure disorder and further on the occurrence of any unwanted stimulation side effects.

Electrical stimulation of the brain is thus a unique tool to perturb endogenous neural signals, allowing the evaluation of neural processes involved in cognitive processing. The present systems and methods provide a new way that stimulation can be employed to selectively improve or disrupt a variety of cognitive processes.

The field of neurostimulation has for many years sought to affect underlying neural processes in disease states using invariant focal patterned stimulation (constant current, constant frequency signal delivered to a single brain focus). No physiological process in the brain occurs this way, so it is not surprising that such an approach has had limited impact in affecting higher brain functions. Indeed with the exception of movement disorders (STN or GPi targets), there is little to no effect of such stimulation on disease states such as epilepsy, memory deficit, psychiatric illness and language or visual impairment. Despite billions of dollars spent on human trials of neuromodulation, limited progress has been made in modulating cognitive processes in humans.

The innovation on which the invention is based is to approach brain stimulation from a network perspective, rather than from a purely focal perspective. Saliently, these methods comprise first to record endogenous neural activity that is individually specific and strongly correlated with the desired cognitive process and indexed against observed behavior. Stimulation will then echo this recording using complex patterns that vary in frequency (indeed may be composed of multiple frequencies) and amplitude (current strength) and will be delivered to the components of the network that are most engaged in the process of interest. In some instances stimulation could also be targeted based on maps of activity generated from a population of other humans, or directed by functional imaging techniques such as fMRI.

This approach to neurostimulation is innovative in that engages and facilitate interactions between multiple brain regions (that may be widely distributed rather than focal). Such stimulation targets multiple brain areas in the functional networks rather than a single area in isolation. This approach has the potential to the field of human neuromodulation and to treat a whole host of disorders such as psychiatric illness, memory deficits, speech difficulty, post retinal blindness etc. Specifically, brain areas that comprise the critical parts of the network that needs to be modulated, to facilitate any of—language, emotion, memory or sensorimotor function, would be targeted based on either of the following: anatomical landmarks, co-registration of the individual brain to a population map of the function of interest, functional activation studies (e.g. fMRI) or direct invasive recordings with depth or subdural grid electrodes in these cases. Electrodes placed in the parts of the network would then be stimulated based on recordings of endogenous activity during the "desired" state or using measures of what would be desirable from recordings made in other individuals. For instance, if a speech area in the frontal lobe called Broca's area is seen to communicate with a temporal lobe language area in a particular frequency band, to enable reading of a piece of text, stimulation of those two sites in the same frequency, to result in the same neural activity and the same connectivity, would facilitate neural decoding of written words. This will be targeted to improve function for individuals where these two regions are disconnected from each other by injury. In another example, if three areas of the brain are involved in a given process, and one is lost due to disease, recordings and interactions between the other two, coupled with stimulation that would mimic the normal function of the missing part, would be used as a neuroprosthetic strategy.

Approximately three million Americans suffer from epilepsy, and about a third of these are medically intractable (Centers for Disease Control and Prevention (CDC. "Epilepsy in adults and access to care—United States, 2010." MMWR. Morbidity and mortality weekly report, 2012, 61(45): 909). Mesial temporal lobe epilepsy (MTLE) represents about forty percent of all epilepsies in adults, with a prevalence rate of 1.7 per 1000 people.

Up to twenty five percent of all MTLE may have bilateral involvement and the seizures in most of these patients are resistant to drug therapies (Hirsch et al., 1991). Some patients with MTLE may be candidates for focal resection, however, the structures that are targeted by these resections—the hippocampus and adjoining entorhinal cortex are also crucial to the retrieval of episodic memory and their destruction often leads to a decline in cognitive function. This issue is particularly of concern in patients with bilateral mesial temporal lobe epilepsy or those who have poor memory reserve—i.e. poor memory function at baseline prior to surgical intervention.

In a particular embodiment, those with medically intractable mesial temporal lobe epilepsy with poor memory function. These patients have either independent bilateral mesial temporal involvement in the genesis of their particular intractable epilepsy, or a rapid spread of seizures from the side of origin to the relatively uninvolved contralateral homolog. Several etiologies can result in bilateral hippocampal epilepsy, including but not limited to herpes encephalitis, cerebral ischemic-anoxic syndromes, mesial temporal sclerosis. Such patients are a significant constituent of the patient population in most major epilepsy programs.

Few therapeutic approaches are available for the patients today and the combination of poor memory function with frequent seizures combined result in a severely disabling illness.

Neurostimulation has been proposed as a possible strategy to modulate epilepsy in those cases where there are no reasonable resective approaches. Current approaches to neuromodulation (e.g. NeuroPace) however show only mild improvement with a median efficacy rate of around fifty percent.

At this time there is only one existent FDA approved and commercially available technology for neuromodulation in epilepsy—the NeuroPace system. In the pivotal study, the efficacy of stimulation by this device in stopping all seizures was very limited and only about half of all patients showed any improvement. Thus, more effective methods for neuromodulation to control seizures are needed, and would have an enormous societal benefit. In addition, there is currently a major focus in academia and in industry for the development of "smarter" neuromodulatory approaches and an increased awareness that stimulation affects not just a focus in the brain but a distributed network. This work will not only help in elaborating the epilepsy network in mesial temporal lobe epilepsy (MTLE), but will also broadly facilitate the development of miniaturized, efficient and effective devices for chronic intracranial recordings and closed loop neuromodulation.

Structured co-activation at higher frequencies tends to strengthen connections (long-term potentiation, LTP), whereas slower more-randomly structured activation tends to weaken connections (long-term depression, LTD). In particular low-frequency (around 1 Hz) trains of paired stimulation pulses have been shown to produce long lasting decreases in connection strength. Paired pulses are thought to activate LTD by activating synapses a second time during their absolute refractory periods. Firstly, stimulation for depressing abnormal excitability should be carried out using low frequencies. Secondly, stimulation should use paired pulses applied in temporal proximity to the interval when the epileptic network is hyper-synchronized. Stimulation should occur following interictal epileptiform discharges (IEDs). Finally, stimulation should be spatially structured to optimally weaken epileptogenic connections. This may be achieved by using stimulation pulses spatially focused based on the obvious seizure network as well as its more remote connections. In the past few decades, the growth of intracranial recording techniques performed chiefly for the localization of epilepsy provides unique datasets with very high spatial and temporal resolution. These data yield new insights into the neurophysiological processes underpinning these complex brain operations that have been studied with techniques without such resolution in the past. During cognitive processes brain regions communicate with each other at very high rates using a variety of frequencies, not unlike a network of computers or cell phones. These communications can be manifest as either a synchronization of the phase of low frequency waves/oscillations (Delta—1-4 Hz; Theta 4-8 Hz or Alpha 8-14 Hz) or a change in power (increase or decrease) in high frequency activity (Beta 14-30 Hz) or Gamma (30-500 Hz). These latter high frequencies correlate with the activity around individual brain cells and are indicators of local processing. They are now widely believed to closely reflect the underlying cognitive, visual or sensori-motor process that a brain region is performing.

Given that most cognitive processes are linked to high frequency gamma (60-250 Hz) oscillations, understanding when these oscillations occur and in which brain area drives which at what point in time is key to optimizing success of neuromodulatory approaches. 4 dimensional maps of cognitive operations are therefore critical not just to understanding complex brain dynamics, but for effective and precise neuro-modulation. In some instantiations, the high frequency oscillations are linked to lower frequency theta and delta frequency oscillations and phase locked stimulation to modulate or reset the phase in two interconnected regions may be useful in modulating some functions such as memory. In other processes such as prefrontal control, beta power changes may also be associated with long range coupling. Therefore a variety of frequencies may be used as potential targets for network based neuromodulation.

In its clinical implementation, recordings will be performed during the healthy/desired state of the system—say in the language system during successful proper name retrieval or in the prefrontal cortex during appropriate control over an adverse affective stimulus—and this will then be replayed into the brain to induce this desired cognitive state. Such stimulation may be timed to ongoing neural activity or to environmental cues. The replay will use multiple frequencies and multiple nodes in the network of interest may be targeted stimulated in patterns to replicate the endogenous activity to replicate the cognitive process of interest. Modulation may also involve using changes in amplitude, direction of information flow, alteration in connectivity, frequency to change the type of processing in the brain and to augment or alter the endogenous activity. Some variation of this type of network based stimulation may even be used to completely suppress undesired activity—examples might be hyperactive systems like in obsessive compulsive disorder or post traumatic stress disorder or the occurrence of epilepsy, as exemplified below.

Specifically, using iEEG data from MTLE patients with relatively preserved memory functions, failed recall is associated with reduced network connectivity compared to successful retrieval. The system and methods described aim at a network modulation that can reverse aberrant, or pathologic, network activity to improve memory functions in intractable MTLE patients.

Successful modulation of memory networks would have immediate benefits for patients with impaired memory not just from epilepsy (potentially also be extendable to patients with unilateral TLE) but also for other classes of patients with prominent memory impairment—e.g. Alzheimer's Disease. It would also make it possible to contemplate targeting specific nodes in the memory network in patients with focal injury (e.g. brain injuries) or particularly distressing memories (e.g. post-traumatic stress disorder).

The described system and methods of network neuromodulation on the memory system will be assessed by using the Hopkins Verbal Learning Test and the outcomes on seizures will be assessed using the Engel and ILAE scoring systems. Ideally investigators would like to see an improvement in seizure outcomes in all patients and seizure freedom for prolonged intervals in the majority of patients PLUS significant improvements in memory performance. Improvement in either of these domains (memory or epilepsy) would carry significant potential for socio-economic benefit in this population as well.

Further embodiments include systems and methods of targeting specific nodes in the memory network in patients with focal injury (e.g. brain injuries) or particularly distressing memories (e.g. post-traumatic stress disorder). The effects brought on by network neuromodulation on the memory system will be assessed using the Hopkins Verbal Learning Test and the outcomes on seizures will be assessed using the Engel and ILAE scoring systems. Ideally one will observe an improvement in seizure outcomes in all patients and seizure freedom for prolonged intervals in the majority of patients as well as significant improvements in memory performance. Improvement in either of these domains (memory or epilepsy) would be a significant socio-economic benefit in this patient population.

In some embodiments, these systems will involve collecting and analyzing data from patients with semi-chronically implanted intracranial electrodes using a variety of approaches including phase coupling (Watrous et al., 2013), amplitude envelope correlations in the gamma band and short term direct directed transfer functions (Korzeniewska et al., 2003) to characterize, among others the network involved in spatial and temporal order recall in humans using intracranial electrodes. In some embodiments, the role of the implanted intracranial electrodes can be supplanted by implanted microchips (e.g. implantable microelectrodes, combined with a receiver/controller) which are stimulated to generate signal.

In some embodiments, networks that are "deranged" during the retrieval of episodic memories will be modulated in their activity to restore them to normal physiology. It is anticipated that the restoration of normal physiological memory function and the successful modulation of the epilepsy in such patients will proceed side by side.

Targets for such recording and neuromodulation include the hippocampus, entorhinal cortex, the dorsolateral prefrontal cortex (DLPFC), inferior parietal lobule and the retrosplenial parietal cortex (at the junction with the posterior cingulate). Targets will be defined in each patient using pre-implantation event related functional MRI (erfMRI) data that will contrasted for correct vs. incorrect memory performance. Aberrant connectivity has been noted in patients with MTLE using DTI tractographic estimates of hippocampal output and using a population study that quantifies such aberrant connectivity in patients will delineate the potential regions of interest for targeting with the implanted electrodes.

In the inventors experience with the RNS® NeuroPace system (Mountain View Calif., USA) they implanted the device into three patients with bilateral MTLE right after the device received FDA approval. This experience provided them with the expertise to select the optimal candidates for intervention and to accomplish the implantation with a minimal probability of adverse events.

Spectral fingerprinting and multiplexing in memory retrieval is illustrated in FIG. 1. In FIG. 1(a), the network exhibits stronger phase synchronization at a lower frequency band (1-4 Hz) for retrieval of spatial information and at a higher frequency band (7-10 Hz) for retrieval of temporal information (Watrous et al., 2013). In FIG. 1 (b), the same network is involved in retrieval of spatial and temporal memory, but nodes communicate via selective frequency bands for distinct types of information.

An image of a patient with a NeuroPace device in place is shown in FIG. 2. The patient in FIG. 2 was diagnosed with bilateral MTLE and mesial temporal sclerosis (MTS), and had two electrodes placed along the long axis of the hippocampus for chronic recording and closed loop neuromodulation. However, no significant improvement was noted in either seizure frequency or memory function in this individual after six months of stimulation at multiple contacts.

Data obtained using fMRI will be used to derive memory networks and to quantify connectivity using graph theoretical models as described for example in (Watrous et al., 2014) and these approaches are used to generate subject specific maps of connectivity both from the fMRI data and the ECoG data as well. Correct vs. incorrect and spatial vs. temporal fMRI retrieval networks are illustrated in FIG. 3. Task-related fMRI and graph theory demonstrate higher connectivity for correct vs. incorrect retrieval and different connectivity for spatial vs. temporal retrieval.

The network stimulation concept is illustrated in FIG. 4. FIG. 4(a) illustrates a simplified network with three nodes: hippocampus (HPC), parahippocampus (PHG) and prefrontal cortex (PFC). HPC has direct projections to and from PHG, but not with PFC. FIG. 4(b) illustrates hypothetical phase vectors and their coherence among these regions. As shown, "successful retrieval" requires coherent oscillations. In the "endogenous phase", these regions are less likely to be in-phase with one another when the network is not engaged. "Stimulation of HPC" will reset the endogenous oscillatory phase (dotted lines) of HPC as well as nodes directly connected with it, i.e., PHG, to a new phase (solid line) Yet, it would take synchronized "Stimulation of HPC and PFC" to bring the network into a coherent phase optimized for task performance.

FIG. 5 illustrates an embodiment of an externalized closed loop system in which the electrons hardware and computers are optimized to record ongoing brain activity and then replay the signal back to the brain to "induce" cognitive processes artificially.

FIG. 6 illustrates a map demonstrating how networks are constructed using stimulation-induced theta phase coherence changes. In the first column "a", the theta coupling network shows significant theta phase coherence increases from baseline. In the second column "b", the theta decoupling network represents significant theta phase coherence decreases from baseline. The hotness of the edge colors represents the edge weights (ranges from 0-1, see color bars), and the size of the nodes represents node degree. The stimulation target nodes are filled shown in 'pink'. In the third column "c", the stimulation had mixed effects on the connectedness of target nodes.

In FIG. 6, columns "a" and "b" provide an overview of the theta phase coherence changes induced by stimulation during stimulation 'on' trials. Column "a" shows a network constructed based on the significant increases of theta phase coherence compared to baseline (coupling). Column "b" is based on the significant decreases from baseline (decoupling). Importantly, relative degrees of coupling and decoupling of the stimulated nodes were not consistent across nodes and patients (see column "c"). In three out of six stimulated nodes, stimulation induced greater theta decoupling than coupling (IPG3 in patient 2, both targets in patient 3), but the other three targets exhibited an opposite pattern. This suggests that stimulation had mixed focal effects on the theta coherence connectivity of the target nodes. It is noteworthy that these target nodes were initially chosen as stimulation targets based on their strong connectivity (node degree) in the spatial retrieval network from baseline recording. Thus the present results suggest theta-burst stimulation to these nodes made that strong connectivity even stronger in some cases, but weakened these nodes' connectedness in other cases.

As described herein are systems and methods of utilizing neurostimulation of a broad network to activate multiple nodes to stimulate successful recall. These systems and methods are based on the concept that poor memory function and the intractable epilepsy in these patients are two sides of the same coin and involvement of crucial substrates for memory production by epileptic processes precludes their availability for normal cognitive operations. Specifically, derangement of the memory networks by epileptogenic process results in the clinically manifested memory deficit.

Described herein are systems and methods that provide a network based neurostimulation approach as the optimal strategy to modulate both the epilepsy as well as the memory deficit in these cases. In order to accomplish this, individual specific memory networks with patterned network stimulation are targeted at multiple loci (nodes) simultaneously using implanted electrodes, such as, but not limited to, for example, subdural electrodes (SDEs) and depth electrodes (DEs), that have been placed in a patient's brain Various physiological issues, such as, for example, blood and fluid accumulation underneath the craniotomy flap, may lead to a non-linear deformation of the brain surface and of an electrode array on post-operative CT scans, and may adversely impact the accurate localization of electrodes located underneath the craniotomy. Prior methods that localize electrodes based on their identification on a post-implantation CT, with co-registration to a pre-implant MRI may further result in significant problems with accuracy of the electrode localization.

The precise localization of implanted electrodes is also generally essential both for clinical purposes as well as for research purposes, such as, for example, in integrating estimates from other imaging data sets like functional MRI (fMRI), positron emission tomography (PET), single photon emission computed tomography (SPECT) and/or magnetoencephalography (MEG). Additionally, the growing field of neural prosthetics also depends very greatly on precise estimates of where in the brain data is being collected from, or where stimulation for neuromodulation is being delivered. The precise placement of probes for sampling or providing biologic or chemical materials into the brain is also dependent on the delineation of cortical targets and optimization of trajectories (akin to those use for DE placement) to attain maximal coverage/sampling with minimal risk of vascular injury. One such precise method of placing such electrodes is described, for example in U.S. application Ser. No. 14/656,117. The present invention relates to systems and methods for stimulating multiple nodes using implanted electrodes, such as, for example, subdural electrodes (SDEs) and depth electrodes (DEs) or microchips that have been placed in a patient's brain.

An evaluation of patients can be performed in order to establish the ability of electrostimulation at multiple nodes to enhance patient cognitive processes, such as but not limited to increased memory, reduced memory loss, and/or maintained memory. The patient parameters measured will typically be similar to those used to assesses Alzheimer's patients and may be selected from the group consisting of: Mini-Mental State Examination (MMSE) level; Alzheimer's Disease Assessment Scale—Cognitive Subscale level; Clinical Dementia Rating-Sum of Boxes (CDR) level; Alzheimer's Disease Study Consortium—Activities of Daily Living level; Clinicians Interview-Based Impression of Change Plus Caregiver Input (CIBIC-plus) level; Neuropsychiatric Inventory (NPI) level; Electro Encephalography (EEG) signal, level or result of EEG signal analysis; PET image data or data analysis; fMRI image data or data analysis; MRI image data or data analysis such as hippocampal volume; and combinations of these.

In one embodiment, the first result comprises an MMSE score, the threshold comprises an MMSE value of 20, and the patient is defined as a candidate if the first result is greater than or equal to the first threshold. A second threshold may be included, such as an MMSE value of 29, and the patient is defined as a candidate if the first result is less than or equal to the second threshold. Alternatively or additionally, a patient parameter result may be an ADAS-cog score, such as when the patient is a candidate when the ADAS-cog score is less than or equal to an ADAS-cog score threshold of 20.

In another embodiment, the first result comprises a CDR score and the threshold is a set of values including 0.5 and 1.0, and the patient is a candidate for direct brain stimulation therapy when the first result is included in these values.

In yet another embodiment, the first result comprises data obtained in a PET scan, such as data selected from the group consisting of: glucose utilization data; PET Pittsburgh compound B (PIB) data; and combinations of these.

After a patient is acceptably screened for direct brain stimulation therapy, a direct brain stimulator is implanted. In one embodiment, an MRI procedure is performed, such as to locate the fornix target for stimulation. The direct brain stimulator may include a stimulating electrode, such that the electrode is positioned to stimulate the Papez Circuit of the patient's brain. In one embodiment, the electrode is positioned 2 mm anterior and parallel to the vertical portion of the fornix within the hypothalamus. Alternatively or additionally, one or more electrodes may be implanted such that the ventral-most contact is 2 mm above the dorsal surface of the optic tract, approximately 5 mm from the midline.

Direct brain stimulation energy may be delivered at a frequency between 20 and 200 Hz, typically 130 Hz. Voltage is typically applied between 1.0 and 10.0V, such as between 3.0 and 3.5V, and more typically less than 7.0V. Energy is delivered using pulse width modulation, such as with multiple pulses of 45-450 μseconds duration, such as with 90 μsecond pulses.

During or after direct brain stimulator implantation, one or more stimulation parameters may be optimized, such as parameters that avoid patient discomfort such as sweating; hallucinations; visual sensations; tingling; and combinations of these. EEG, magnetoencephalography or other neurophysiologic data may be recorded and analyzed to optimize stimulation parameters. A PET scan may be performed, such as to record blood flow and/or produce FDG data. The stimulator portion (e.g. one or more electrodes) may have implantation position confirmed such as via an MRI.

Direct brain stimulation therapy may include the delivery of one or more drugs or other agents, such as a cholinesterase inhibitor. A confirmation of drug tolerance, and/or a titration of drug dose may be performed.

According to another aspect of the invention, a method of implanting a direct brain stimulator in a patient to treat cognitive function is provided. A patient imaging procedure is performed collecting at least one patient image. A direct brain stimulator, including at least one stimulation element, is implanted. The at least one stimulation element is positioned at a stimulation location that is based on the at least one patient image.

One or more imaging procedures or techniques can be used, such as imaging procedures selected from the group consisting of: MRI; functional MRI (fMRI) X-ray; ultrasound imaging; PET scanning; and combinations thereof. Multiple imaging procedures can be performed at different times, such as imaging procedures performed more than a week apart. These two images may be compared to determine any change in brain size; brain shape; brain thickness; and combinations of these.

Numerous stimulation elements can be used singly or in combination with other stimulation elements. Typical stimulation elements include but are not limited to: electromagnetic elements such as electrodes and magnets; optical stimulation elements such as visible or infrared light sources; and chemical stimulation elements such as an element configured to deliver biologically active molecules, neurotransmitters and/or neurotrophic factors.

A calibration or titration procedure may be performed during or after direct brain stimulator implantation. The direct brain stimulation implantation may be halted, or the direct brain stimulator removed if already implanted, under certain conditions, such as inability to complete a calibration or titration procedure. Typically calibration or titration procedures may adjust parameters selected from the group consisting of: electromagnetic energy delivery such as voltage or current delivered; light delivery such as wavelength or magnitude of light delivered; chemical parameters such as concentration of chemical delivered or rate of chemical delivery; and combinations of these. Alternatively or additionally, stimulator removal may be prompted by encountering a particular patient condition or state such as chest pain; labored breathing; twitching; unacceptable EKG signal; or unacceptable EEG signal. Other undesired patient conditions include but are not limited to: unacceptable neurological level of paranoia; psychosis; anxiety; or confusion. Multiple stimulation elements may be repositioned, during or after direct brain stimulator implantation, such as to maximize or minimize a patient parameter. In one embodiment, a stimulation element is repositioned to maximize recalled memory or memories. Alternatively or additionally, a stimulation element may be repositioned to minimize one or more of: chest pain; labored breathing; twitching; unacceptable EKG signal; unacceptable EEG signal; or an adverse neurological condition such as an unacceptable level of paranoia, psychosis, anxiety, or confusion.

According to another aspect of the invention, a method of optimizing stimulation parameters of a direct brain stimulator implanted in a patient to treat cognitive function is provided.

In some aspects, the present systems and methods provide for the application of multifocal neurostimulation to enhance cognitive processes. In particular, the present invention provides direct brain stimulation to increase memory, reduce memory loss, and/or maintain memory. In some embodiments, a method for implanting a direct brain stimulator in a patient to treat cognitive function, the method comprising: performing a patient imaging procedure and collecting at least one patient image; implanting a direct brain stimulator, the stimulator comprising at multiple stimulation elements; wherein the stimulation elements are positioned at multiple stimulation locations based on patient imaging, such as MRI; x-ray; ultrasound imaging; fMRI; PET; and combinations thereof.

Prophetic Example

Target Population Selection:

Patients will be carefully selected from those that are referred for surgical intervention or evaluated for drug resistant epilepsy on the basis of meeting criteria for bilateral mesial temporal lobe epilepsy and marked memory impairment. Video-EEG monitoring will be used to identify patients with bilateral inter-ictal spikes and ictal onset patterns consistent with a temporal lobe seizure onset. The subjects MRI scans will be used to quantify the structural derangements of the medial temporal lobe as well. Whole-brain MPRAGE MRis and high-resolution oblique coronal T2-weighted turbo-spin echo (TSE) and FLAIR weighted scans will be used for high-resolution hippocampal imaging, as described in [36-40]. Hippocampal subregional boundaries will also be defined based on anatomical guidelines, as described in Amaral et al., 1990. In patients where there is no clear imaging abnormalities in the medial temporal lobe, or in those where the electro-clinical syndrome is not well defined by scalp recordings alone, bilateral stereo-electro-encephalographic (SEEG) evaluation is the standard clinical approach at our institution to identify candidacy for surgical interventions. Patients identified as having bilateral MTLE by SEEG will also be enrolled into the cohort.

To quantify memory and other cognitive function, a core battery of standardized clinical neuro-psychological tests will be used, most of which they receive as part of their clinical evaluation. The battery includes the Mini-Mental State Exam, Wechsler Abbreviated Scale of Intelligence, Wechsler Memory Scale, Boston Naming Test, Word Fluency, Wisconsin Card Sorting Test, Trail Making Test, Finger Tapping Test, Beck Depression Inventory, and Hamilton Anxiety Rating Scale. The standard neuropsychological criterion for defining aselective memory impairment will be quantified as a difference score of more than two standard deviations on the Wechsler Memory Scale-Revised (WMS-R, Delayed Index) compared to a healthy population. Patients with evidence of significant medical disease, major psychiatric problems, dementia or substance abuse will be excluded. Once patients are enrolled, the effects of stimulation on memory will be examined using the Hopkins Verbal Learning Test [34], a list learning test which has 6 alternate forms. For non-verbal memory, the Non-Verbal Selective Reminding Test (Plenge et al., 1996), which involves memory for a single dot in a field of 5 dots. Alternate forms are created by changing the target dot for each session, thus creating 5 alternate forms. Using a within-subjects design alternating stimulation (on) and non-stimulation (off) periods for each subject and administering each test during the 'on' and 'off' periods, as well as pre- and post-tests. A reliable change index (Christensen and Mendoza, 1986), is calculated based on published data for each test and using a 95% criterion to determine if a significant increase or decrease in memory function has occurred from one period to the next. All subjects will be exposed to each test in the pre-test period and alternate forms will be used to minimize practice effects during 'on' and 'off' testing periods. It is anticipated that an increase in the memory score between 'off' and 'on' periods and decrease between 'on' and 'off' periods for patients with low (<-2 SO) pre-test scores and no change for patients who did well on one of the tests.

Study Oversight and Monitoring:

Following IDE approval from the FDA to implant these 8 patients given that there are no meaningful options available to help with their memory function or their epilepsy at the current time. The data safety monitoring board at UTHealth will meet monthly to review the progress of each patient enrolled into the study. This panel will comprise of a neurosurgeon, a neurologist, an ethicist and a statistician. They will review the specifics of each patient after enrollment and prior to study procedures. Reviews after implantation, and monthly after modulation has begun will be carried out. Specifically the metrics of seizure frequency and memory performance will be tabulated to present to this committee.

The Medtronic Activa RC+S system is designed to allow for measurement of key electrophysiology in a neurostimulator. This capability allows the characterization of neural networks and observation of patient response to stimulation. The network access is provided by a modular design that supports up to 4 4-contact electrodes, which can each be independently placed through stereotactic neurosurgery. The electrophysiology is enabled with a next generation preamplifier that can multiplex to all 16 contacts and process up to four bipolar channels simultaneously (Cong et al., 2012). Data can be processed internally to the device with a custom DSP, logged internally for short epochs [order of 5 min], and/or telemetered through a MICS-band transceiver to an external data hub. Stimulation is independently controlled on the 16 contacts. The networks can be sampled using this tool, with a protocol that supports up to 10 hours of continuous streaming from four channels sampled at 1 kHz. A short recharge interval of roughly 30 minutes is then required, but the streaming can stay operational during this process. Different bipolar pairs can be explored to identify the optimal networks for chronic study. For the second phase of the study, the embedded DSP processor supports the creation of a seizure detector to identify the networks correlated with seizure activity. For the final phase of the study, the electrophysiology capabilities and embedded DSP can be used to explore the response of the network to paired-pulses and theta stimulation provided by the stimulation circuitry.

The investigational Activa RC+S system is designed to allow for measurement of key electrophysiology in a neurostimulator. This capability allows the researcher to characterize neural networks and observe their response to stimulation. The network access is provided by a modular design that supports up to 4 4-contact electrodes, which can each be independently placed through stereotactic neurosurgery. The electrophysiology is enabled with a next generation preamplifier that can multiplex to all 16 contacts and process up to four bipolar channels simultaneously (Centers for Disease Control and Prevention (CDC. "Epilepsy in adults and access to care—United States, 2010." MMWR. Morbidity and mortality weekly report, 61(45): 909, 2012). Data can be processed internally to the device with a custom DSP, logged internally for short epochs [order of 5 min], and/or telemetered through a MICS-band transceiver to an external data hub. Stimulation is independently controlled on the 16 contacts. For the first phase of this proposal, the networks can be sampled using this tool, with a protocol that supports up to 10 hours of continuous streaming from four channels sampled at 1 kHz. A short recharge interval of roughly 30 minutes is then required, but the streaming can stay operational during this process. Different bipolar pairs can be explored to identify the optimal networks for chronic study. For the second phase of the study, the embedded DSP processor supports the creation of a seizure detector to identify the networks correlated with seizure activity. For the final phase of the study, the electrophysiology capabilities and embedded DSP can be used to explore the response of the network to paired-pulses and theta stimulation provided by the stimulation circuitry.

Study Design:

The investigational Activa RC+S system (Medtronic, USA) and 4 separate depth electrodes with 4 recording/stimulating channels in each hemisphere (bilateral implants in all cases) will be implanted in 8 patients over the study interval. Patients will undergo an erfMRI to delineate areas of activation during successful encoding and recall. Tractographic and resting state fMRI data will also be compiled for the cohort. Electrode placement will be generally stereotypic to target the episodic memory networks as described above but optimized to each individual's fMRI activation. Once the device is implanted the patients will undergo the following.

Characterization of the Seizure Network:

Once the electrodes are implanted patients will undergo baseline continuous recordings to isolate the contacts maximally involved in inter-ictal spiking and in seizure onsets. This recording will be carried out with 4 selected channels at a time sampling at 400 Hz and allowing for the system to transmit the data wirelessly and be recharged once a day. This process will be carried out to allow recordings from all channels in gray matter (it is anticipated that despite most optimal; targeting, around 25% of the recording contacts will be located in white matter) over 6-8 weeks, after which the most active 4 contacts in each hemisphere (total 8 per patient) will be recorded from, for the subsequent month. The electrophysiology is enabled with a next generation preamplifier in the Activa RC+S that can multiplex to all 16 contacts and process up to four bipolar channels simultaneously, as described in Cong et al., 2014. Data can be processed internally to the device with a custom DSP, logged internally for short epochs [order of 5 min], and/or telemetered through a MICS-band transceiver to an external data hub.

Characterization of the Memory Network:

A modification of a paradigm used extensively to assay memory for contextual details (i.e., "source" memory) in humans as described in (Addante et al., 2011; Cansino et al., 2002; Davachi and Wagner, 2002; Mitchell and Johnson, 2009; Wagner et al., 2005) will be implemented. In the system described, participants encode objects by imagining them within a specific spatial or temporal context that they describe prior to the experiment, which they then attempt to retrieve following item recognition. All objects will be normalized for frequency and associability. During encoding, if a participant is presented with a picture of a "faucet," on a spatial trial, they will be asked to imagine this object within a familiar spatial context (e.g., a location within a familiar kitchen). On a temporal trial, in contrast, they will be asked to place this item within a timeline of events in their life (e.g., a faucet that they used at some point in their lives). Following the imagination period for each trial, they will be asked to rate their ability to place the object within the cued context. At retrieval, participants will see words or objects that they encountered during encoding as well as novel "lure" items that they did not encode. Participants will indicate with a button press whether they viewed the object previously or not. Following their response, they will be prompted with a question about whether they encoded the details of that object within a specific spatial or temporal context. A version of the same paradigm with distinct stimuli will also be used for the erfMRI data collection prior to the implantation.

Network Modulation for Seizure Suppression:

There are two goals for network modulation—facilitating coupling between regions that are not well coupled during memory performance and uncoupling regions that are hyper-synchronized during as part of the seizure network. Spatio-temporally structured stimulation has been shown to induce long-term changes in the strength of connections between individual neurons in vitro and in vivo (Feldman 2009; Collingridge et al., 2010). In particular low-frequency (around 1 Hz) trains of paired stimulation pulses have been shown to produce long lasting decreases in connection strength (Collingridge et al., 2010). Paired pulses are thought to activate long-term depression (LTD) by activating synapses a second time during their absolute refractory periods. This suggests three factors for stimulation that might result in LTD of the hyperexcitable seizure network for the proposed project. Firstly, stimulation for depressing abnormal excitability should be carried out using low frequencies. Secondly, stimulation should use paired pulses applied in temporal proximity to the interval when the epileptic network is hyper-synchronized. Stimulation should occur following interictal epileptiform discharges (IEDs). Finally, stimulation should be spatially structured to optimally weaken epileptogenic connections. This could be achieved by using stimulation pulses spatially focused based on the obvious seizure network as well as its more remote connections. The embedded DSP processor in the Activa RC+S supports the creation of a seizure detector to identify the networks correlated with seizure activity.

Network Modulation for Memory Improvement:

Given that successful memory retrieval relies on oscillatory coherence among multiple medial temporal and neo-cortical regions, inducing such network coherence via electrical stimulation may improve the retrieval. Indeed, many studies have sought to improve memory function by applying trans-cranial (e.g., TMS, tDCS) or intracranial (DBS) stimulation, but mostly reported detrimental effects or mixed results across subjects. Stimulating one node, and at arbitrary times relative to ongoing processes, may have disturbed endogenous network communication rather than improving the network coherence. In contrast, multi-site stimulation that induces and drives coherent oscillation in the network nodes will improve the memory retrieval in MTLE patients Delivery of theta stimulation to the distributed components of the memory network is anticipated to enable closer binding when this network is involved in memory processes. The electrophysiology capabilities and embedded DSP in the Activa device can be used to explore the response of the network to paired-pulses and theta stimulation provided by the stimulation circuitry.

Once stimulation has begun memory performance is quantified monthly using the Hopkins Verbal Learning Test (Brandt 1991), a list learning test which has 6 alternate forms. The Non-Verbal Selective Reminding Test (Plenge et al., 1996) which involves memory for a single dot in a field of 5 dots will be used to characterize non-verbal memory. Alternate forms are created by changing the target dot for each session, thus creating 5 alternate forms and preventing overlearning of the stimuli. The same channels identified in above during both successful and unsuccessful memory function are recorded. The network models for both of these states will be generated as will measures of coupling/directed information between any two recording contacts during these epochs.

Although the invention has been described with respect to specific embodiments thereof, these embodiments are merely illustrative, and not restrictive of the invention. The description herein of illustrated embodiments of the invention, including the description in the Abstract and Summary, is not intended to be exhaustive or to limit the invention to the precise forms disclosed herein (and in particular, the inclusion of any particular embodiment, feature or function within the Abstract or Summary is not intended to limit the scope of the invention to such embodiment, feature or function). Rather, the description is intended to describe illustrative embodiments, features and functions in order to provide a person of ordinary skill in the art context to understand the invention without limiting the invention to any particularly described embodiment, feature or function, including any such embodiment feature or function described in the Abstract or Summary. While specific embodiments of, and examples for, the invention are described herein for illustrative purposes only, various equivalent modifications are possible within the spirit and scope of the invention, as those skilled in the relevant art will recognize and appreciate. As indicated, these modifications may be made to the invention in light of the foregoing description of illustrated embodiments of the invention and are to be included within the spirit and scope of the invention. Thus, while the invention has been described herein with reference to particular embodiments thereof, a latitude of modification, various changes and substitutions are intended in the foregoing disclosures, and it will be appreciated that in some instances some features of embodiments of the invention will be employed without a corresponding use of other features without departing from the scope and spirit of the invention as set forth. Therefore, many modifications may be made to adapt a particular situation or material to the essential scope and spirit of the invention. The disclosures of all patents, patent applications and publications cited herein are hereby incorporated herein by reference, to the extent that they are consistent with the present disclosure set forth herein.

Reference throughout this specification to "one embodiment", "an embodiment", or "a specific embodiment" or similar terminology means that a particular feature, structure, or characteristic described in connection with the embodiment is included in at least one embodiment and may not necessarily be present in all embodiments. Thus, respective appearances of the phrases "in one embodiment", "in an embodiment", or "in a specific embodiment" or similar terminology in various places throughout this specification are not necessarily referring to the same embodiment. Furthermore, the particular features, structures, or characteristics of any particular embodiment may be combined in any suitable manner with one or more other embodiments. It is to be understood that other variations and modifications of the embodiments described and illustrated herein are possible in light of the teachings herein and are to be considered as part of the spirit and scope of the invention.

In the description herein, numerous specific details are provided, such as examples of components and/or methods, to provide a thorough understanding of embodiments of the invention. One skilled in the relevant art will recognize, however, that an embodiment may be able to be practiced without one or more of the specific details, or with other apparatus, systems, assemblies, methods, components, materials, parts, and/or the like. In other instances, well-known structures, components, systems, materials, or operations are not specifically shown or described in detail to avoid obscuring aspects of embodiments of the invention. While the invention may be illustrated by using a particular embodiment, this is not and does not limit the invention to any particular embodiment and a person of ordinary skill in the art will recognize that additional embodiments are readily understandable and are a part of this invention.

At least a portion of embodiments discussed herein can be implemented using a computer communicatively coupled to a network (for example, the Internet), another computer, or in a standalone computer. As is known to those skilled in the art, a suitable computer can include a central processing unit ("CPU"), at least one read-only memory ("ROM"), at least one random access memory ("RAM"), at least one hard drive ("HD"), and one or more input/output ("I/O") device(s). The I/O devices can include a keyboard, monitor, printer, electronic pointing device (for example, mouse, trackball, stylist, touch pad, etc.), or the like.

ROM, RAM, and HD are computer memories for storing computer-executable instructions executable by the CPU or capable of being complied or interpreted to be executable by the CPU. Suitable computer-executable instructions may reside on a computer readable medium (e.g., ROM, RAM, and/or HD), hardware circuitry or the like, or any combination thereof. Within this disclosure, the term "computer readable medium" or is not limited to ROM, RAM, and HD and can include any type of data storage medium that can be read by a processor. For example, a computer-readable medium may refer to a data cartridge, a data backup magnetic tape, a floppy diskette, a flash memory drive, an optical data storage drive, a CD-ROM, ROM, RAM, HD, or the like. Software implementing some embodiments disclosed herein can include computer-executable instructions that may reside on a non-transitory computer readable medium (for example, a disk, CD-ROM, a memory, etc.). Alternatively, the computer-executable instructions may be stored as software code components on a direct access storage device array, magnetic tape, floppy diskette, optical storage device, or other appropriate computer-readable medium or storage device.

Any suitable programming language can be used to implement the routines, methods or programs of embodiments of the invention described herein, including the custom script. Other software/hardware/network architectures may be used. For example, the software tools and the custom script may be implemented on one computer or shared/distributed among two or more computers in or across a network. Communications between computers implementing embodiments can be accomplished using any electronic, optical, radio frequency signals, or other suitable methods and tools of communication in compliance with known network protocols. Additionally, any signal arrows in the drawings/figures should be considered only as exemplary, and not limiting, unless otherwise specifically noted. Based on the disclosure and teachings provided herein, a person of ordinary skill in the art will appreciate other ways and/or methods to implement the invention.

As used herein, the terms "comprises," "comprising," "includes," "including," "has," "having," or any other variation thereof, are intended to cover a non-exclusive inclusion. For example, a process, product, article, or apparatus that comprises a list of elements is not necessarily limited only those elements but may include other elements not expressly listed or inherent to such process, process, article, or apparatus.

Furthermore, the term "or" as used herein is generally intended to mean "and/or" unless otherwise indicated. For example, a condition A or B is satisfied by any one of the following: A is true (or present) and B is false (or not present), A is false (or not present) and B is true (or present), and both A and B are true (or present). As used herein, including the claims that follow, a term preceded by "a" or "an" (and "the" when antecedent basis is "a" or "an") includes both singular and plural of such term, unless clearly indicated within the claim otherwise (i.e., that the reference "a" or "an" clearly indicates only the singular or only the plural). Also, as used in the description herein, the meaning of "in" includes "in" and "on" unless the context clearly dictates otherwise.

As used herein, "patient" or "subject" includes mammalian organisms, such as human and non-human mammals, for example, but not limited to, rodents, mice, rats, non-human primates, companion animals such as dogs and cats as well as livestock, e.g., sheep, cow, horse, etc. Therefore, for example, although the described embodiments illustrate use of the present methods on humans, those of skill in the art would readily recognize that these methods and compositions could also be applied to veterinary medicine as well as on other mammals.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.
U.S. application Ser. No. 14/656,117
U.S. Patent Application No. 2013/0289385
U.S. Patent Application No. 2014/0350634
U.S. Pat. No. 6,920,359
U.S. Pat. No. 8,024,049
U.S. Pat. No. 8,412,332
U.S. Pat. No. 8,649,876
U.S. Pat. No. 8,944,985
WO 2004/037342
WO 2014/0180358
WO 2015/0148863
WO 8644940
Addante et al., Prestimulus theta activity predicts correct source memory retrieval. Proceedings of the National Academy of Sciences of the United States of America, 108(26): p. 10702-7, 2011.
Amaral and Insausti, The Hippocampal formation, in *The Human Nervous System*. G. Paxinos, Editor. Academic Press: San Diego, p. 711-755, 1990.
Brandt, The Hopkins Verbal Leaning Test: Development of a new memory test with six equivalent forms. The Clinical Neuropsychologist, 5, pp. 125-142, 1991.
Cansino et al., Brain activity underlying encoding and retrieval of source memory. Cereb Cortex, 12(10): p. 1048-56, 2002.
Centers for Disease Control and Prevention (CDC. "Epilepsy in adults and access to care—United States, 2010." MMWR. Morbidity and mortality weekly report, 61(45): 909, 2012.
Christensen and Mendoza, "A method of assessing change in a single subject: an alteration of the RC index." *Behavior Therapy* 17:305-308, 1986.
Collingridge et al., "Long-term depression in the CNS." *Nature reviews: Neuroscience*, 2010.
Cong et al., "A 32-channel modular bi-directional neural interface system with embedded DSP for closed-loop operation," in European Solid State Circuits Conference (ESSCIRC), ESSCIRC 2014-40th, vol., no., pp. 99-102, 22-26 Sep. 2014.
Davachi and Wagner, Hippocampal contributions to episodic encoding: insights from relational and item-based learning. J Neurophysiol, 88(2): p. 982-90, 2002.
Feldman, "Synaptic mechanisms for plasticity in neocortex," Annual Review of Epilepsia Neuroscience, 2009.
Hirsch, et al., Comparison of bitemporal and unitemporal epilepsy defined by depth electroencephalography. Annals of neurology, 30(3): 340-346, 1991.
Korzeniewska et al., Determination of information flow direction among brain structures by a modified directed transfer function (dDTF) method. Journal of Neuroscience Methods, 125(1-2): 195-207, 757, 2003.
Mitchell and Johnson, Source monitoring 15 years later: what have we learned from fMRI about the neural mechanisms of source memory? Psychol Bull, 135(4): p. 638-77, 2009.
Plenge et al., Nonverbal selective reminding test: Efficacy in the assessment of adults with temporal lobe epilepsy. *Journal of Epilepsy*, Vol. 9, Issue 1, pp. 65-69, April 1996.
Wagner et al., Parietal lobe contributions to episodic memory retrieval. Trends in Cognitive Sciences, 9(9): p. 445-53, 2005.
Watrous and Ekstrom, The spectro-contextual encoding and retrieval theory of episodic memory. *Frontiers in Human Neuroscience*, 8, 75. http://doi.org/10.3389/fnhum.2014.00075, 2014.
Watrous et al., Frequency-specific network connectivity increases underlie accurate spatiotemporal memory retrieval. Nature Neuroscience, 16(3): 349-356, 2013.

What is claimed is:

1. A method of enhancing a cognitive process in a subject having a disease or neurological injury, the method comprising applying an intracranial electrical stimulation to a plurality of nodes in different regions of the brain of the subject, wherein the intracranial electrical stimulation is applied at nodes in different regions of the brain of the subject that are active during an effective cognitive process, wherein:
  the different regions of the brain of the subject comprise a first region of the brain in a hippocampus (HPC) region, a second region of the brain in a parahippocampal (PHG) region, and a third region of the brain in a prefrontal cortex (PFC) region; and
  applying the intracranial electrical simulation to the plurality of nodes comprises:
    applying a first electrical signal to a first node in the first region of the brain;
    applying a second electrical signal to a second node in the second region of the brain;
    applying a third electrical signal to a third node in the third region of the brain; and
    inducing coherent oscillations between the first, second and third nodes.

2. The method of claim 1, further comprising monitoring a cognitive process of the brain.

3. The method of claim 1 wherein applying the intracranial electrical simulation is phase-synchronized at a first frequency band.

4. The method of claim 1 wherein applying the intracranial electrical simulation to the plurality of nodes in different regions of the brain of the subject induces coherent oscillations between the nodes.

5. The method of claim 1 wherein application of the first electrical signal, the second electrical signal and the third electrical signal to the first node, the second node and the third node is phase-synchronized at a first frequency band.

6. The method of claim 1 wherein the first, second and third nodes comprise subdural electrodes (SDEs) or depth electrodes (DEs).

7. The method of claim 1 further comprising:
performing an imaging procedure to obtain an image of the brain of the subject; and
identifying the different regions of the brain of the subject that are active during the effective cognitive process.

8. The method of claim 7 wherein identifying the different regions of the brain of the subject that are active during the effective cognitive process comprises using anatomical landmarks or population maps of brain activity or placing intracranial electrodes to localize and characterize brain areas engaged in a given cognitive process.

9. The method of claim 7 wherein the imaging procedure is selected from the group consisting of: magnetic resonance imaging (MRI), functional magnetic resonance imaging (fMRI), x-ray, ultrasound imaging, and positron emission tomography (PET).

10. The method of claim 1 further comprising:
performing an imaging procedure to obtain an image of a non-subject brain; and
identifying the different regions of the non-subject brain that are active during the effective cognitive process.

11. The method of claim 1 wherein the intracranial electrical simulation has a frequency between 20 and 200 Hz.

12. The method of claim 1 wherein the intracranial electrical simulation has a voltage between 1.0 volts and 10.0 volts.

13. The method of claim 1 wherein the intracranial electrical simulation has a current value between 0.01 mA and 20 mA.

14. The method of claim 1 wherein the intracranial electrical simulation current is either based on voltage or current, based on the specific area being stimulated.

15. The method of claim 1 wherein the intracranial electrical simulation has a pulse width of 45-450 μs (microseconds).

16. The method of claim 1 wherein the intracranial electrical simulation has a pulse width of approximately 90 μs (microseconds).

17. The method of claim 1 wherein the effective cognitive process comprises spatial recall, temporal recall, speech production, reading comprehension, language comprehension, arithmetic comprehension, attention control, cognitive control, coordinated locomotion or sensory feedback related to movement.

18. The method of claim 1, wherein the intracranial electrical stimulation applied to the plurality of nodes is used for the modulation of epilepsy.

* * * * *